United States Patent [19]

Birch et al.

[11] 3,949,751

[45] Apr. 13, 1976

[54] METHOD AND DEVICE FOR DISPENSING MEDICAMENT TO THE BODY

[75] Inventors: Leslie William Birch, Desborough; Desmond Alfred Dean, Beeston, both of England; Harry Howell, deceased, late of Castle Donnington, England, by Eunice Cockburn Gray, executor

[73] Assignee: Fisons Limited, London, England

[22] Filed: Aug. 26, 1974

[21] Appl. No.: 500,471

Related U.S. Application Data

[63] Continuation-in-part of Ser. No. 127,493, March 24, 1971, abandoned.

[30] Foreign Application Priority Data

Mar. 3, 1970 United Kingdom............... 14544/70

[52] U.S. Cl. ................. 128/266; 128/208; 222/193
[51] Int. Cl.²................. A61M 15/08; A61M 13/00
[58] Field of Search ........... 128/265, 266, 206, 208, 128/231, 232, 260, 216

[56] References Cited
UNITED STATES PATENTS

| 1,300,654 | 4/1919 | Rose ................................... 128/266 |
| 2,180,063 | 11/1939 | McKinley............................ 128/231 |
| 2,501,279 | 3/1950 | Kark .................................... 128/266 |
| 2,519,555 | 8/1950 | Fields.................................. 128/266 |
| 2,946,332 | 7/1960 | Sacks.................................. 128/266 |
| 2,992,645 | 7/1961 | Fowler............................. 128/266 X |
| 3,094,988 | 6/1963 | Dunmire............................. 128/216 |
| 3,831,606 | 8/1974 | Damani........................... 128/208 X |

FOREIGN PATENTS OR APPLICATIONS

| 94,040 | 2/1897 | Germany ............................ 128/265 |
| 604,276 | 5/1960 | Italy..................................... 128/265 |

Primary Examiner—Aldrich F. Medbery
Attorney, Agent, or Firm—Wenderoth, Lind & Ponack

[57] ABSTRACT

A nasal insufflator for powdered medicaments comprises a tubular body having a longitudinal air passageway. One end of the body has an end suitable for insertion into a nostril, the other end is provided with a squeeze bulb by which a stream of air is driven through the passageway and into the nostril of a user. Wholly within the body and intermediate its ends is a chamber into which can be placed a capsule of powdered medicament. The device is characterised by having a piercing means, eg a needle, which is reciprocable along the axis of the passageway by having its non-operative end mounted upon the inner wall of the bulb. Longitudinal depression of the bulb drives the piercing end of the piercing means through the end walls of a capsule mounted in the chamber. Release of the bulb draws the piercing end back to its non-operative position, thus leaving the capsule pierced and ready to be emptied by transverse depression of the bulb.

9 Claims, 2 Drawing Figures

METHOD AND DEVICE FOR DISPENSING MEDICAMENT TO THE BODY

BACKGROUND OF THE INVENTION

The present invention relates to a method and device for dispensing medicaments in finely divided form and is a continuation-in-part of our Application Ser. No. 127,493 filed Mar. 24, 1971 (now abandoned).

It has been proposed to dispense medicaments in finely divided form by means of powder puffers in which the medicament is contained in a rubber squeeze bulb or bottle and is dispensed merely by squeezing the bulb. However, such devices are unsatisfactory for many uses in that there is no control over the amount of medicament dispensed. It has therefore been proposed to supply the medicament in the form of unit doses put up in capsules, cartridges or other small containers. However, one then has to provide some means whereby the container can be pierced or ruptured before the medicament is available for use. To do this it has been proposed to provide squeeze bulb type insufflators with an external socket or chamber in which the container is mounted and to provide this socket or chamber with a fixed pin which pierces the container as the container is forced home.

However, these forms of device are unsatisfactory in that the pin is used to hold the container in place in the socket and in many instances can be exposed and cause damage to a user when the device is not in use, e.g., when carried in a users pocket.

SUMMARY OF THE INVENTION

We have now devised a device in which the piercing means can be retracted to a safe position when not in use and yet can be actuated and retracted by a simple mechanism using the compression and expansion of the squeeze bulb. Furthermore, the piercing means in our device does not hold the container in position in the chamber and the container can be a loose fit within the chamber so that the airflow generated by the squeeze bulb flows around the container as well as through it. This aids dispersion of the medicament particles in the air stream.

The present invention therefore provides a device for dispensing medicament in finely divided form from a container containing such medicament, which device comprises:

1. an elongated housing having a longitudinal passageway therethrough, one end of the housing being provided with a pump means for driving air through the passageway, the other end of the housing being adapted for insertion into an aperture in a human body;
2. a chamber adapted to receive the container of medicament, said chamber being located wholly within the housing and intermediate the ends of the housing, the chamber being intersected by the passageway;
3. an elongated piercing means extending into the pump means and having an operative piercing end for piercing that end adjacent to the pump means of a container mounted within the chamber, the piercing end being reciprocable substantially along the longitudinal axis of the housing from a normally non-operative position to an operative piercing position; and
4. mounting means located within the said pump means whereby the non-piercing end of the piercing means is mounted inside the pump means, which mounting means is reciprocable by actuation of the pump means substantially along the longitudinal axis of the piercing means, whereby the piercing means may be driven from its normally non-operative position to its operative position along the intended direction of flow of air through the device.

BRIEF DESCRIPTION OF THE DRAWINGS

Other features of the invention will be apparent from the following detailed description, taken with the accompanying drawings, wherein.

DETAILED DESCRIPTION OF THE INVENTION

Figures 1, 2:
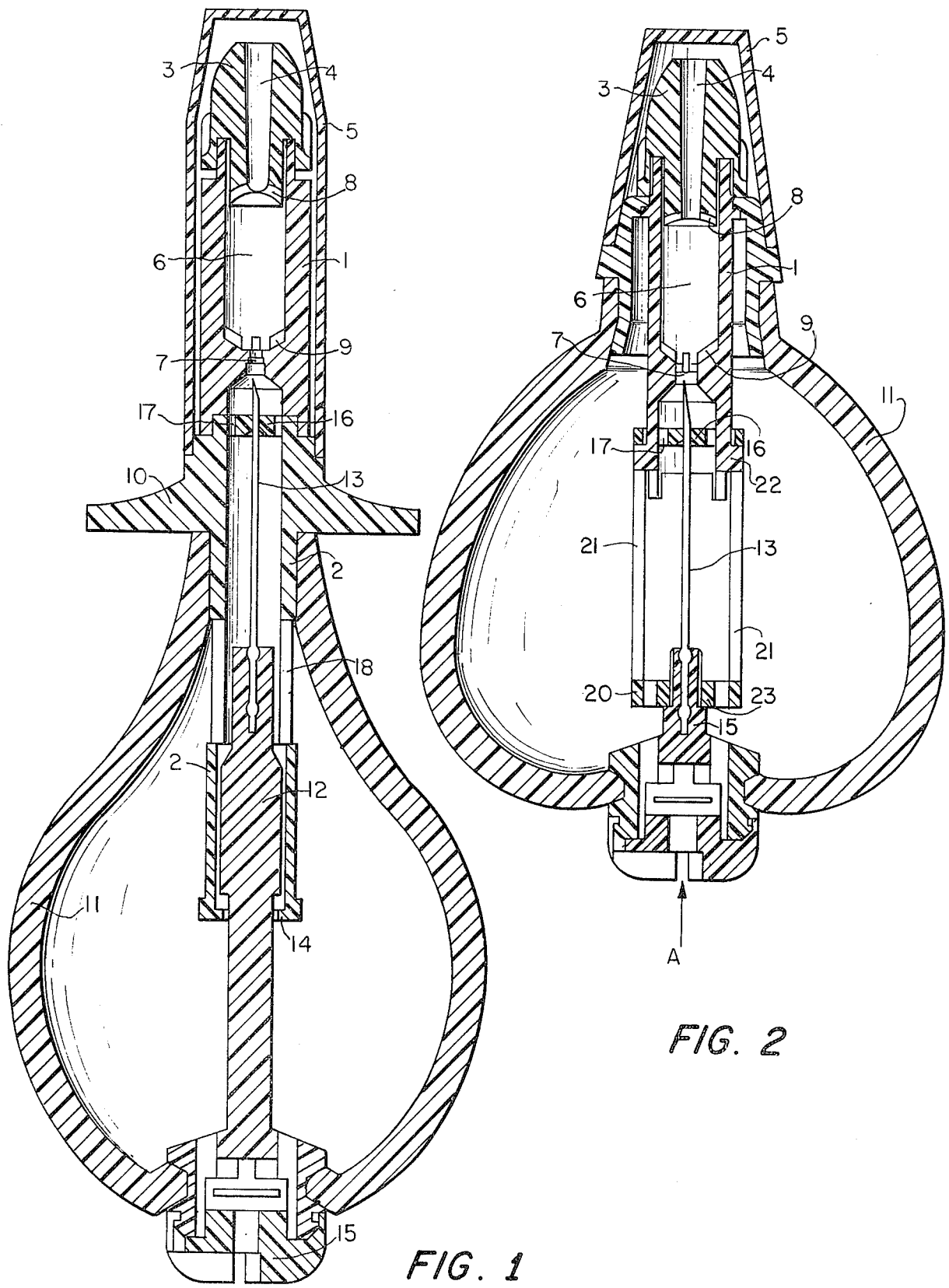
FIG. 1 is a longitudinal section of a first embodiment of the present invention.
FIG. 2 is a longitudinal section of a second embodiment of the present invention.

A preferred form of the device will now be described by way of illustration only with regard to FIG. 1 of the accompanying drawings.

The device comprises a cylindrical housing, in this case formed in two parts 1 and 2 for moulding reasons, having a central longitudinal airway therethrough. The free end of part 1 is provided with a medicament dispensing device, such as a detachable nose piece 3 having a central outlet 4, adapted for insertion into the opening of a body cavity. If desired a cap 5 may be provided for nose piece 3 and part 1. A chamber 6 is formed within part 1 by internal narrowing of the airway to a narrow bore 7, so as to form one end wall of the chamber 6, and by dishing the end of nose piece 3 mounted upon part 1. The dimensions of the chamber 6 are such that a capsule or cartridge which is intended to mount therein is a loose fit so that air may flow over as well as through the cartridge. It is preferred to provide the end walls of chamber 6 with radial grooves 8 and 9 to aid the flow of air across the end of the capsule or cartridge and to prevent blockage of the inlet and outlet bores 7 and 4 by the capsule or cartridge itself. Typically the chamber 6 is from 0.01 to 0.050 inches larger in diameter than the capsule or cartridge to be used therein and grooves 8 and 9 have a depth of about 0.02 inches.

Part 2 of the housing is provided with two external finger grips 10 and carries a squeeze bulb 11 made from rubber or other resilient material. A large proportion of part 2 extends into the body of bulb 11. Within part 2 is journalled a cylindrical holder 12 for a piercing needle 13. The holder 12 is free to slide up and down within the airway in part 2 and is prevented from escaping from the airway by the annular flange 14 on the free end of part 2. Holder 12 is extended longitudinally beyond part 2 to a mounting block 15 which is a spring fit in a hole cut in the base of bulb 11. The needle 13 held in holder 12 extends towards chamber 6 and is supported by a disc 16 mounted at the chamber end of part 2 by means of ribs 17. Preferably the disc 16 and ribs 17 are formed integrally with part 2. Desirably the apertures around disc 16 formed by ribs 17 are from 0.025 to 0.06 inches in depth radially. The side walls of part 2 within the bulb 11 are cut with slots 18 whereby air may pass from bulb 11 to the passageway in parts 1 and 2. Mounting block 15 preferably incorporates an air inlet whereby air may be drawn into the bulb. Desirably the air inlet comprises a non-return valve, e.g. of the rubber disc type.

The airway in parts 1 and 2, chamber 6 and its inlet and outlet, the disc 16, the needle 13, the holder 12 and the bulb 11 share a substantially common longitudinal axis and the device is dimensioned so that when the device is at rest, i.e. the bulb is not depressed, the free piercing end of the needle 13 lies on the bulb side of chamber 6, and when the bulb is longitudinally depressed the free piercing end of needle 13 lies within chamber 6 or beyond.

In use, a user removes nose piece 3 and inserts a capsule or cartridge of medicament into chamber 6 and replaces nose piece 3. In order to pierce the cartridge or capsule, the user longitudinally depresses the bulb 11, e.g. by gripping finger pieces 10 and pressing on the external face of block 15. This drives holder 12 up the airway of piece 2. The free piercing end of needle 13 is thus driven from its non-operative position (as shown in the drawing) up into chamber 6 to pierce at least that end of the container closest to the bulb. The forward travel of needle 13 is halted when holder 12 or block 15 buts against a suitably positioned stop, e.g. when block 15 buts against the end of part 2. Where both ends of the capsule or cartridge are to be pierced the free end of needle 13 must clearly pass through chamber 6. However, where only one end needs to be pierced (e.g. when capsules having one end prepierced are used) the free end of needle 13 need only travel into but not through chamber 6. We prefer that the needle 13 pierce both ends of the capsule or cartridge since this results in capsules or cartridges having piercing flaps which are inclined in the direction of flow of air through the device and therefore are not liable to be blown closed during use, leading to ineffective dispensing of the medicament.

After piercing the capsule or cartridge by depressing the bulb, the user releases the bulb 11 which then returns to its normal shape. Preferably the bulb 11 is held in slight tension by ensuring that holder 12 buts against flange 14 before the bulb is fully relaxed. As the bulb returns to its normal shape the bulb will automatically retract holder 12 and needle 13 to the position shown in the drawings. The device is now ready for use and powder is dispensed by depressing the bulb, preferably transversely, to generate an air stream through chamber 6 which entrains medicament from the capsule or cartridge. Longitudinal depression of the bulb is also effective, but there may be a risk that the user will obstruct the air inlet to bulb 11, and we therefore prefer to provide the external surface of block 15 with intersecting air feeder grooves.

The above form of device provides a simple and effective means by which medicament may be dispensed and which overcomes the problems of earlier devices associated with exposed piercing means. As indicated above the loose fit of the medicament container aids powder entrainment as does the fact that piercing of the container is along the direction of flow of air through the device. We have also found that with the above device the disc 16 in which the needle 13 is journalled reduces the suck back of medicament into the bulb 11. It appears that much of the powder sucked back lodges around the piercing member and is then displaced back into chamber 6 when the bulb 11 is squeezed.

The above form of the device may be modified in a number of ways and an alternative form of device is shown in FIG. 2 in which parts similar to those for the device of FIG. 1 are denoted by the same numerals. In this form of device the needle 13 is mounted directly in block 15 and the movement of needle 13 guided by means of a tubular member 20 which slides over the exterior of part 1 (part 2 being dispensed with) and the guide disc 16 which is now mounted within the bulb end of the passageway in part 1. The tubular member 20 comprises a cylindrical sleeve having longitudinal slots 21 in which lugs 22 on the outside of part 1 engage. Member 20 is mounted on the needle mounting by a transverse end member 23. This device offers a more compact construction than the device shown in FIG. 1 but operates in essentially the same way.

As indicated above, the devices shown in FIGS. 1 and 2 may be modified in a number of other ways. Thus, in place of a squeeze bulb, the airstream could be generated by a piston and cylinder pump arrangement; and the end of holder 12 need not be fixed to block 15 but could merely be provided with a pad which bears against the inner surface of the bulb 11 under the influence of a spring.

The shape of the housing member is not critical, but it is conveniently substantially tubular, and finger grips or corrugations to faciliate the holding and/or operation of the device may be provided on its exterior if desired. The housing may be formed of any suitable material such as metal, for example steel, or a plastics material such as nylon, rigid polyethylene, or polystyrene. The removable nose piece may be mounted on the housing by a screw thread, by one or more co-operating ribs and grooves on the housing and nose piece, by frictional engagement, by an external or internal catch, or by any other suitable means.

The restriction in the airway in part 1 forming one end wall of the chamber 6 may be formed integrally with the walls of part 1 or may be a separate member, e.g. an annular ring having radial projections by which it is mounted in part 1.

The orientation of the container for the medicament is not critical, but it is preferred that an axis of symmetry of the container, if such exists, lies substantially along the longitudinal axis of the housing. In the case of capsules and like containers having a long axis, this long axis is preferably disposed substantially along the long axis of the housing.

The perforating means is suitably formed from a stainless steel or carbon steel which may be plated, for example, with nickel or chromium, or coated, for example, with a plastics material to inhibit corrosion or to lubricate passage of the needle through the capsule. It has been found that in order to obtain optimum perforation of a gelatine capsule, the piercing end of the piercing member should not be sharpened to a conventional conical point but should be sharpened with a plane face at an acute angle. The piercing member is preferably of sufficient length to pierce both ends of the container though this is not necessary when a container having a preformed upper perforation is used.

In the form of device described above, the capsule or container of medicament is restrained in chamber 6 by the dished interior surface of nose piece 3 which provides a stop against which the container and bears during piercing. However, a separate stop may be provided if desired. It is desirable that the container have approximately 0.02 to 0.1 inches of longitudinal freedom of play when in position in chamber 6 so that the container is a loose but restrained fit within the chamber.

We claim:

1. A device for dispensing medicament in finely divided form from a container containing such medicament, which device comprises:

an elongated housing having a longitudinal passageway therethrough, one end of said housing being provided with a collapsible bulb for driving air through said passageway, the other end of the housing having medicament dispensing means for insertion into an opening of a body cavity;

a chamber adapted to receive the container of medicament, said chamber being located wholly within said housing and intermediate the ends of said housing, said chamber being intersected by said passageway;

means for piercing a container mounted within said chamber and comprising an elongated piercing needle having an operative piercing end for piercing that end adjacent to the said collapsible bulb of a container mounted within said chamber, said piercing end being reciprocable substantially along the longitudinal axis of the housing from a normally non-operative position to an operative piercing position; and mounting means attached to the collapsible bulb and located within said collapsible bulb for mounting the non-piercing end of said piercing needle within and attaching said non-piercing end to said collapsible bulb, said mounting means being reciprocable by compression of said collapsible bulb substantially along the longitudinal axis of the piercing needle, whereby said piercing needle may be driven from its normally non-operative position to its operative position along the intended direction of flow of air through the device.

2. A device as claimed in claim 1, wherein said passageway, said chamber, said piercing needle and said bulb share a substantially common axis.

3. A device as claimed in claim 1, wherein said medicament dispensing means at said other end of said housing comprises a removable nose-piece, which provides access to said chamber.

4. A device as claimed in claim 1, further comprising a container mounted in a loose but restrained fit within said chamber.

5. A device as claimed in claim 1, wherein the end walls of said chamber are each provided with a groove adapted to provide a flow of air across a perforation in a container when positioned within said chamber.

6. A device as claimed in claim 1, wherein said perforating needle is dimensioned to pass through said chamber.

7. A device as claimed in claim 1, wherein said perforating needle passes through a perforated disc mounted within said passageway between said chamber and said mounting means.

8. A device as claimed in claim 1, wherein the length of said needle being such that when in said operative piercing position said piercing end does not extend substantially beyond and out of said chamber.

9. A method for administering a powdered medicament to a patient, said method comprising:

providing a device comprising:

an elongated housing having a longitudinal passageway therethrough, one end of said housing being provided with a collapsible bulb for driving air through said passageway, the other end of the housing having medicament dispensing means for insertion into an opening of a body cavity;

a chamber adapted to receive the container of medicament, said chamber being located wholly within said housing and intermediate the ends of said housing, said chamber being intersected by said passageway;

means for piercing a container mounted within said chamber and comprising an elongated piercing needle having an operative piercing end for piercing that end adjacent to the said collapsible bulb of a container mounted within said chamber, said piercing end being reciprocable substantially along the longitudinal axis of the housing from a normally non-operative position to an operative piercing position; and mounting means attached to the collapsible bulb and located within said collapsible bulb for mounting the non-piercing end of said piercing needle within and attaching said non-piercing end to said collapsible bulb, said mounting means being reciprocable by compression of said collapsible bulb substantially along the longitudinal axis of the piercing needle, whereby said piercing needle may be driven from its normally non-operative position to its operative position along the intended direction of flow of air through the device;

positioning a container of finely divided medicament within said chamber;

compressing said bulb longitudinally, thus moving said bulb longitudinally from said non-operative position toward said chamber to said operative position, and piercing said container, releasing the longitudinal compression on said bulb and returning said needle to said non-operative position;

inserting said medicament dispensing means into the opening of a body cavity; and compressing said bulb, thereby forcing air through said passageway and into said chamber, and forcing medicament from the pierced container through said medicament dispensing means and into said body cavity opening.

* * * * *